United States Patent [19]

Stein et al.

[11] 4,071,533
[45] Jan. 31, 1978

[54] PHOSPHORAMIDATES AND THIOPHOSPHORAMIDATES AS PESTICIDES

[75] Inventors: Robert George Stein, Kenosha, Wis.; Terry Lee Couch, Waukegan, Ill.

[73] Assignee: Abbott Laboratories, North Chicago, Ill.

[21] Appl. No.: 665,975

[22] Filed: Mar. 11, 1976

[51] Int. Cl.$^2$ .................... C07D 333/12; A01N 9/36
[52] U.S. Cl. .................... 260/332.5; 260/329 P; 260/330.5; 260/551 P; 424/202; 424/217; 424/220
[58] Field of Search .............. 260/329 P, 551 P, 332.5

[56] References Cited
U.S. PATENT DOCUMENTS

| 2,964,528 | 12/1960 | Wicker et al. | 260/329 P |
| 3,018,215 | 1/1962 | Pianka | 260/329 P |
| 3,478,057 | 11/1969 | Baklien et al. | 260/329 P |

OTHER PUBLICATIONS

Hartough, "The Chem. of Hetero. Compounds; Thiophene and Deriv." (1952) p. 29.

*Primary Examiner*—Alan M. Siegel
*Attorney, Agent, or Firm*—Paul D. Burgauer; Robert L. Niblack

[57] ABSTRACT

Compounds of the formula

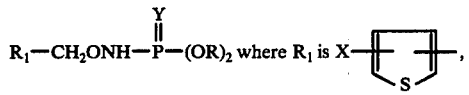

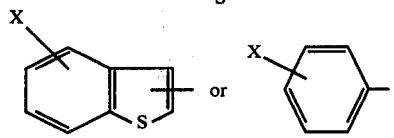

and X is hydrogen, halo, alkyl, cyano or nitro, Y is oxygen or sulfur and R is lower alkyl, have been found to be excellent pesticides.

5 Claims, No Drawings

PHOSPHORAMIDATES AND THIOPHOSPHORAMIDATES AS PESTICIDES

DESCRIPTION OF THE INVENTION

This invention relates to compounds useful as pesticides. More particularly, it relates to novel phosphoramidates or thiophosphoramidates useful as pesticides.

The compounds of this invention are characterized by the formula

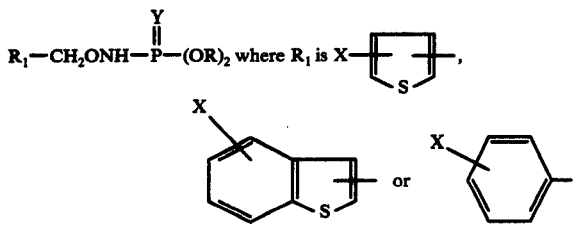

and X is hydrogen, halo, alkyl, cyano or nitro, Y is oxygen or sulfur and R is lower alkyl.

The term "alkyl" as used herein refers to both straight and branched chain alkyl radicals having 1 to 8 carbon atoms and which include methyl, ethyl, n-butyl, n-pentyl, iso-pentyl, hexyl and the like.

The term "halo" includes chlorine, fluorine, bromine and iodine.

The compounds of this invention exhibit pesticidal activity and are effective in the range of 125 to 2500 ppm.

The inventive compounds are prepared by the following general method:

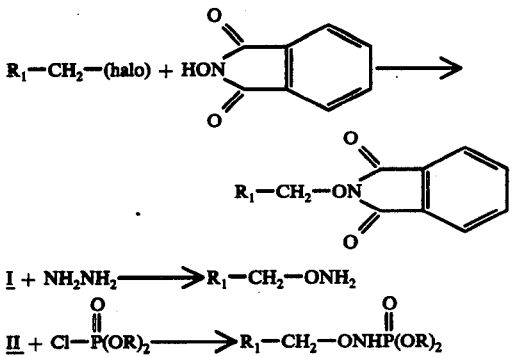

wherein Y, R and $R_1$ have the above meaning.

The $R_1CH_2$(halo) compounds are prepared by classical methods described in the literature. They can be prepared by halomethylation on an aromatic system (J. V. Braun & J. Nelles, Ber. 67 (1094) 1934), halogenation of an aromatic methyl group using N-haloimides and amides (A. Wohl, Ber. 52 (51) 1919, Ber. 54 (476) 1921) or from the corresponding alcohols using hydrochloric acid, thionyl chloride, phosphorus oxychloride or any of the other halogenating reagents.

The active halo compounds so obtained are reacted with N-hydroxyphthalimide using acetonitrile as the solvent and triethylamine as the acid acceptor. This leads to the oxyphthalimide compounds of structure I. In turn, the compounds of structure I are reacted with hydrazine in ethanol to give the oxyamines of structure II. The oxyamine derivatives II are then reacted with appropriate phosphorylating agents which leads to the novel compounds of this invention (III).

The following examples will serve to further illustrate the preparation of the present compounds and the advantages of the present invention. In all instances, the analytical results for C, H and N were in good agreement with the calculated values of the compounds prepared.

EXAMPLES 1-5 a. A solution of 116 g. (0.70 mole) 5-chloro-2-chloromethyl thiophene in 50 ml. acetonitrile was added to a stirring solution of 70.7 g. (0.70 mole) triethylamine and 114 g. (0.70 mole) N-hydroxyphthalimide in 500 ml. acetonitrile.

The solutiion was slowly brought to reflux temperature. After refluxing for 2 hours, the mixture was cooled and poured to 2000 ml. cold $H_2O$. The solid was filtered and washed with cold water. A small sample was recrystallized from dimethylformamide (hereinafter referred to as DMF) and melted at 164°–165° C. The total yield of crude product was 171 g. This crude material was of sufficient purity to proceed to the next step.

Other compounds found of structure I were prepared by the same method; they are listed in Table I:

b. To a refluxing mixture of 162 g. (0.55 mole) 5-chloro-2-thenyloxyphthalimide in 1000 ml. ethanol was added 32 g. (0.55 mole) 85 percent hydrazine hydrate. Solution occurred after 10 minutes and a precipitate of phthalazine-1,4-dione appeared after 10 more minutes refluxing. The mixture was refluxed two hours, cooled, filtered and the filter cake was washed with 95 percent ethanol. The filtrate was concentrated in vacuo, yielding an oil. The oil distilled at 105–107° C/8mm to give 54.8 g. of 5-chloro-2-thenyloxyamine as a colorless liquid.

Other compounds of structure II were prepared by this method from the compounds of structure I; they are also listed in Table I.

TABLE I

| EXAMPLE | $R_1$ | RECRYSTALLIZATION SOLVENT FOR I | Mp ° C for I | BOILING PT. FOR II |
|---------|-------|-------------------------------|--------------|---------------------|
| 1 | 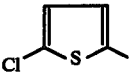 | DMF/$H_2O$ | 164–165 | 105-7/8 mm |
| 2 |  | EtOH/$H_2O$ | 127–128 | 92/10 mm |
| 3 | 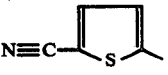 | EtOH/$H_2O$ | 166–167 | 135–7/3.5 mm |

TABLE I-continued

| EXAMPLE | R₁ | RECRYSTALLIZATION SOLVENT FOR I | Mp ° C for I | BOILING PT. FOR II |
|---------|-----|-------------------------------|--------------|--------------------|
| 4 | (methylthiophene group with CH₃) | EtOH | 133–134 | 94–5/5 mm |
| 5 | (benzothiophene group) | Tetrahydrofuran/H₂O | 164–165 | 100–3/0.5 mm |

EXAMPLES 6–14

A solution of 6.88 g. (0.04 mole) diethyl chlorophosphate in 20 ml. benzene was added to a stirring solution of 6.54 g. (0.04 mole) 5-chloro-2-thenyloxyamine and 4.04 g. (0.04 mole) triethylamine in 150 ml. benzene. The mixture was stirred at room temperature for 4 hours. The reaction mixture was washed successively with water, dilute hydrochloric acid and water. The solution was dried over magnesium sulfate, then filtered and the filtrate concentrated in vacuo to an oil. By Kügelrohr distillation, 8.5 g. of colorless oil was obtained, boiling at 180° C/2mm. Other compounds of structure III were made in the same manner; they are listed in Table II.

EXAMPLE 15

To determine the activity of the compounds against various pesticides, the screens described below were used; all percentages given there are percentage by volume where liquids are concerned.

Two-spotted spider mites (*Tetranychus urticae*); spray method One Henderson bush lima bean plant, 8–10 days old, with a 24 hr. infestation of mites was used for each dilution of the chemical tested. The test compounds were initially screened at 2500 ppm. A stock solution of 50,000 ppm of III, made in 25 % DMF and 75 % isopropanol (IPA) with 4 % of a compatible surfactant (Tween 20, marketed by the Atlas Chemical Co.), was diluted to 2500 ppm (1:20) in a diluent consisting of 50% acetone and 50% H₂O with 0.1% Tween ® 20 per 100 ml.

Using a deVilbis-like atomized spray, the top and underside of both leaves were sprayed with approximately 5 ml. of the appropriate dilution using a fine mist. Mortality was recorded after 48 hrs. The results are shown in Table II.

House Fly (*Musca domestica*)

Approximately 50 three-day old adult house flies were used for each dilution of the chemical tested. The test compounds were initially screened at 2500 ppm. A stock solution of 50,000 ppm of III made in 25% DMF and 75% IPA with 4% Tween ® 20 was diluted to 2500 ppm (1:20) using 70% acetone - H₂O as diluent.

Flies were anesthetized with CO₂ and placed in a Büchner funnel. The appropriate dilution was poured onto the flies. Contact time was approximately 5 seconds. The chemical was removed by suction and the flies were then transferred to pint ice-cream containers. These were covered with saran wrap and mortality noted after one hour. The results are shown in Table II.

Cabbage Looper (*Trichopulsia ni*)

Approximately 15 four day old cabbage looper larvae were used for each dilution of the chemical tested. The compounds were intially screened at 2500 ppm. A stock solution of 50,000 ppm made in 25% DMF and 75% IPA with 4% Tween ® 20 was diluted to 2500 ppm (1:20) in a diluent of 70% aqueous acetone.

The larvae were placed in a Büchner funnel. The appropriate dilution was poured onto them. Contact time was approximately 5 seconds. The chemical was removed by suction and the worms were placed in a Petri dish along with a leaf from a Henderson bush lima bean plant. After 24 hours, mortality was determined. The results are shown in Table II.

Ovicide Screen

This test was designed to screen those compounds which may effect embryogenesis of insect and mite eggs. The screening technique described below is able to detect lethal and sub-lethal effects on the eggs themselves and on larvae which hatch from treated eggs. Newly laid cabbage looper eggs (*Trichoplusia ni*) were used in this test.

A fresh egg strip was taken from an appropriate cage of young adult cabbage loopers. This strip was disinfected for 10 minutes in a 10 percent formaldehyde solution. This step was necessary to surface sterilize the eggs to prevent extraneous mortality to newly emerged larvae from viruses and other pathogens. After treatment in the formaldehyde solution, the egg strips were rinsed in running tap water for 30 minutes and then allowed to air dry.

Following drying, the egg strip was cut into one inch squares. One square containing no less than ten eggs was used for each chemical screened.

The new compounds were initially screened at 500 ppm. This initial solution was prepared from a 50,000 ppm. stock dissolved in 25% DMF and 75% IPA with 4% Tween 20. Dilution to 500 ppm. was done with a 70% aqueous acetone.

An egg patch was placed in a Büchner funnel, attached to a vacuum source. Ten milliliter aliquots of the appropriate compound were poured directly onto the patch. The chemical was immediately removed by suction. The egg patch was then allowed to air dry and the number of eggs per patch were recorded. The treated eggs were then placed in a disposable Petri dish (100 × 20 mm.) containing 30 ml. of normal looper rearing media (casein, alfalfa meal and wheat germ diet). A disc of filter paper 11 cm in diameter was placed over the dish. The plastic lid was then pressed over the filter paper to seal the dish. This prevents the escape of the newly hatched first instar larvae. These were then incubated at 30° C ± 1° for 6 days.

To evaluate activity, the number of larvae emerging from each egg patch were counted. These were compared to the number of eggs contained in the patch. Percent mortality was then recorded and is shown in Table II.

TABLE II $$R-CH_2ONH-\overset{\overset{X}{\|}}{P}-(OR)_2$$

| EXAMPLE | $R_1$ | Y | R | Spider Mites 2500 | Spider Mites 250 | Spider Mites 125 | House Fly 2500 | Cabbage Looper 2500 | Ovi-cide 500 | *bp °C |
|---|---|---|---|---|---|---|---|---|---|---|
| 6 | 5-chloro-2-thienyl | O | $C_2H_5$ | M | M | M | M | I | I | 180/2 mm |
| 7 | 5-chloro-2-thienyl | S | $C_2H_5$ | M | M | M | M | M | SL | 140–145/1.5 mm |
| 8 | 2-thienyl | O | $C_2H_5$ | M | Mod | Mod | I | I | SL | 158–162/1 mm |
| 9 | 2-thienyl | S | $C_2H_5$ | M | SL | SL | Mod | I | I | 130–132/1 mm |
| 10 | 5-cyano-2-thienyl | O | $C_2H_5$ | M | I | I | I | I | — | — |
| 11 | 5-methyl-2-thienyl | O | $C_2H_5$ | I | I | I | I | I | — | — |
| 12 | 5-methyl-2-thienyl | S | $C_2H_5$ | I | I | I | I | I | SL | 170/2.5 mm |
| 13 | benzo[b]thienyl | S | $C_2H_5$ | M | I | I | SL | I | — | — |
| 14 | phenyl | S | $C_2H_5$ | M | — | — | I | I | — | 140–147/2 mm |

*Kugelrohr distillation air bath temperatures

Concerning the above Table, the entry M (Marked) refers to a mortality of 76–100%; Mod (Moderate) reflects a mortality of 51–75%; SL (Slight) stands for 26–50%; I (Inactive) stands for 0–25% mortaity. In all instances, higher concentrations showed higher activities and many of the above entries showing inactivity were quite active at concentrations of 10,000 to 50,000 ppm.

Although the above compounds carry primarily chlorine as the X-substituent in formula III, compounds wherein X is Br, I, F or $NO_2$ show substantially the same biological profiles as those whose pesticidal activity has been recited above. They are all made in the fashion as shown above. The compounds of this invention can be used in various areas and for a variety of pests. As pesticidal compositions in general, they are used in the range of 10 to 50,000 ppm; a preferred and usually high range is from 25 to 5,000 ppm. It is to be understood that where applicable and where desired, the compounds may be used in the form of an acid addition salt which may be required when the compounds are used in high concentration in an aqueous medium to increase their solubility or wetability.

The compositions of this invention may be applied in the form of emulsifiable concentrates, powders, granules or dusts. An agronomically acceptable carrier for the purposes of this invention includes any substance which can be used to dissolve, disperse or diffuse the above novel compounds, without impairing the effectiveness of the active ingredient, and which is not deleterious to the soil or the plant in any chemical or physical manner.

In formulating the compositions of this invention, other components may be included to aid in the adsorption or absorption of the active ingredient by the plant. Components such as wetting agents, solubilizers, emulsifiers, humiditants, surfactants and adjuvants are useful for this purpose and may be incorporated in the formulations.

The above compounds are preferably compounded with inert diluents to a liquid or solid composition containing between 10,000 and 200,000 ppm, particularly compositions containing 25,000 to 50,000 ppm. Such stock mixes are easily packagable and stable and can be diluted by the consumer to the necessary concentration for application in the field, i.e. to concentrations of between 125 to 2,500 ppm.

We claim:

1. A compound of the formula

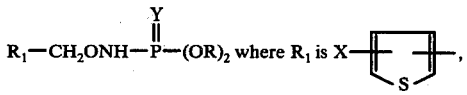

and X is hydrogen, halo, alkyl, cyano or nitro, Y is oxygen or sulfur and R is lower alkyl.

2. The compound according to claim 1 wherein $R_1$ is 5-chloro-2-thienyl, Y is O, and R is lower alkyl.

3. A compound according to claim 2 diethyl-N-(5-chloro-2-thienyl)-phosphoramidate.

4. The compound according to claim 1 wherein $R_1$ is 5-chloro-2-thienyl, Y is S and R is lower alkyl.

5. A compound according to claim 4 diethyl-N-(5-chloro-2-thienyl)-thiophosphoramidate.